US008166734B2

(12) United States Patent
Ruetenik

(10) Patent No.: US 8,166,734 B2
(45) Date of Patent: May 1, 2012

(54) EQUINE COLD THERAPY APPARATUS AND METHOD

(76) Inventor: Monty L. Ruetenik, Clear Lake Shores, TX (US)

( * ) Notice: Subject to any disclaimer, the term of this patent is extended or adjusted under 35 U.S.C. 154(b) by 201 days.

(21) Appl. No.: 12/581,620

(22) Filed: Oct. 19, 2009

(65) Prior Publication Data

US 2010/0095641 A1    Apr. 22, 2010

Related U.S. Application Data

(60) Provisional application No. 61/196,928, filed on Oct. 22, 2008.

(51) Int. Cl.
*B68C 5/00* (2006.01)

(52) U.S. Cl. .................................. 54/82; 168/2

(58) Field of Classification Search ...... 54/82; 119/850; 36/111, 2.6; 168/1–4, 18, 28, DIG. 1
See application file for complete search history.

(56) References Cited

U.S. PATENT DOCUMENTS

| 55,234 | A | | 6/1866 | Bode |
| 92,065 | A | | 6/1869 | Lighthall |
| 3,749,091 | A | * | 7/1973 | Basa .............................. 604/293 |
| 4,456,001 | A | * | 6/1984 | Pescatore ........................ 600/14 |
| 4,587,956 | A | | 5/1986 | Griffin et al. |
| 4,622,035 | A | * | 11/1986 | Palmer et al. ................. 604/293 |
| 4,899,693 | A | * | 2/1990 | Arnold .......................... 119/28.5 |
| 4,961,933 | A | | 10/1990 | Campos Pino |
| 4,981,010 | A | | 1/1991 | Orza et al. |
| 5,152,285 | A | * | 10/1992 | Gnegy ........................... 607/108 |
| 5,209,048 | A | * | 5/1993 | Hanson ............................. 54/82 |
| 5,363,632 | A | * | 11/1994 | Armato .............................. 54/82 |
| 5,658,324 | A | | 8/1997 | Bailey et al. |
| 5,871,458 | A | * | 2/1999 | Detty ............................... 602/27 |
| 6,062,008 | A | * | 5/2000 | Nor .................................. 54/82 |
| 6,139,486 | A | | 10/2000 | Matuszewski et al. |
| 6,238,427 | B1 | | 5/2001 | Matta |
| 6,656,208 | B2 | | 12/2003 | Grahn et al. |
| 7,178,321 | B2 | | 2/2007 | Ruetenik |
| D565,256 | S | | 3/2008 | Ruetenik |
| 7,445,051 | B2 | | 11/2008 | Ruetenik |
| 2002/0074136 | A1 | * | 6/2002 | Wiltz .............................. 168/18 |
| 2005/0028401 | A1 | * | 2/2005 | Johnson .......................... 36/2.6 |
| 2006/0016098 | A1 | * | 1/2006 | Lu et al. .......................... 36/2.6 |
| 2007/0039289 | A1 | * | 2/2007 | LeCompte ........................ 54/82 |
| 2007/0068125 | A1 | * | 3/2007 | Davis ............................... 54/82 |
| 2008/0072453 | A1 | * | 3/2008 | Mizrahi ............................ 36/44 |
| 2008/0156503 | A1 | * | 7/2008 | McSherry ........................ 168/2 |
| 2010/0223893 | A1 | * | 9/2010 | D'Arpe ............................ 54/82 |

OTHER PUBLICATIONS

NEWS, Farrier's Journal, No. 137, Apr. 2009; p. 36-37.
Church, Research Sets Standards for Studying Effects of Cold Therapy, The Horse.com; Jan. 1, 2004, Article 4846.

* cited by examiner

*Primary Examiner* — Rob Swiatek
*Assistant Examiner* — Lisa Tsang
(74) *Attorney, Agent, or Firm* — Douglas Baldwin

(57) ABSTRACT

Apparatus for and methods of core cooling the blood of an equine animal. The apparatus is a flexible boot with an orthotic pad that has various features to allow for circulating coolant so the bottom hoof area of an equine can be cooled. Optionally the pad is designed to allow cooling under vacuum. In some aspects the apparatus also provides elements to facilitate cooling the lower leg of the equine in a way designed to allow coolant circulated through the boot pad to also be circulated through leg cooling elements while maintaining a controlled temperature against the leg surface. The invention is also a method of core cooling an animal utilizing the apparatus described.

18 Claims, 6 Drawing Sheets

EQUINE COLD THERAPY APPARATUS AND METHOD

CROSS REFERENCE TO RELATED APPLICATIONS

This application claims benefit of Provisional Application Ser. No. 61/196,928 filed Oct. 22, 2008.

FIELD OF THE INVENTION

This invention relates to an equine boot and boot-pad assembly useful for treatment of lameness, including laminitis and for enhancing the performance of equine animals. Specifically, it relates to a boot/pad assembly and method to apply cooling and, optionally, reduced pressure to equine hooves to treat hoof disorders and to improve performance.

BACKGROUND

Equine lameness has many causes, of which laminitis is among the most serious. Laminitis, often called founder, is a disease that affects fifteen (15) percent of the horse population and results in debilitation in nearly seventy-five (75) percent of those horses. Despite recent intensive investigation, no cure currently exists, but early detection and prompt treatment can, in most cases, prevent the need for euthanasia. Laminitis is a fast acting disease that attacks and breaks down the connective tissue, the laminae, between the horse's hoof wall and coffin bone. The disease occurs in three successive stages: the developmental, the acute, and the chronic. The developmental stage of laminitis occurs between initiation of the disease and the appearance of acute lameness and lasts a maximum of seventy-two (72) hours. The acute stage can last between four (4) and sixty (60) hours. This means that many horses may be already in the chronic stage of the disease before they receive treatment. Therefore, until an actual cure is found, a feasible method for preventing and treating the disease is needed.

While a cure for laminitis may be in the distant future, recent research on the use of cryotherapy (or cold therapy) as a potential prophylactic offers immediate hope for preventing the disease. Two landmark studies from the Australian Equine Laminitis Research Unit have opened this area of research. Pollitt and Van Eps ((Pollitt, C. C. and Van Eps, A. W. Prolonged, continuous distal limb cryotherapy in the horse. Equine Vet. J. 2004; 36(3): 216-220) initially evaluated the effect of prolonged, continuous cryotherapy to the equine distal limb. They found that continuous cryotherapy was well tolerated and resulted in a marked cooling of the treated foot. In a subsequent study Van Eps and Pollitt determined that distal limb cryotherapy could be used to prevent laminitis induced by alimentary carbohydrate overload. (Van Eps, A. W. and Pollitt, C. C. Equine laminitis: cryotherapy reduces the severity of the acute lesion. Equine Vet. J. 2004; 36(3): 255-260) their results suggest that cryotherapy could be used as a potentially effective prophylactic strategy in horses at risk of developing acute laminitis. Even though cryotherapy has been shown to be a potentially effective strategy, the method used, icing down the horse's leg, is both cumbersome and imprecise. Furthermore, researchers have previously only used cryotherapy on one leg of the test animals for a short time.

It is also known that the application of a vacuum to an injured member, especially together with cryotherapy, is also beneficial in increasing blood flow and, thereby, in healing. Cold therapy applied with reduced pressure has been shown effective in rapidly reducing core temperature of human and animals and in improving performance. Reducing core temperature is useful in treating overheated individuals but has also been shown to increase performance, as is done with athletes. See, for example, U.S. Pat. No. 6,656,208 U.S. Pat. No. 6,156,208 and the references and other patents sited therein. See also products of and information provided by AVAcore Technologies, Inc., 333 Parkland Plaza Drive, Ste. 700, Ann Arbor, Mich. 48103, 333 Parkland Plaza Drive, Ste. 700, Subjecting an injured member to a magnetic field is another technique known to promote healing and prevent soreness. See U.S. Pat. No. 4,587,956, U.S. Pat. No. 6,139,486 and U.S. Pat. No. 6,062,008. These therapies lead to enhanced comfort for horses when being transported and stalled as well relieving and/or preventing development laminitis and related diseases in equine animals. The present invention provides a greatly improved apparatus and method for cryotherapy for animal, especially equine animals.

SUMMARY OF THE INVENTION

The benefits of cooling the blood of an equine are well known. It is beneficial to quickly cool down a heated or overheated animal and cooling of the blood can enhance performance in a performance animal, and the benefit of cooling the hoof and legs during treatment of lameness has been reported.

It is one object of this invention to be able to provide a means for cryotherapy that may easily be applied to all four feet of a horse simultaneously. This is especially useful prior to the onset of laminitis, which may prevent the development of the disease.

It is also an object of this invention to provide an improved means to apply cold therapy, optionally at reduced pressure (vacuum). In addition the boot/pad assembly of this invention may be used to apply copper and magnetic contact to the sole of the hoof.

The present invention is an apparatus and method for economically and efficiently cooling the blood of an equine animal.

This invention is a boot and boot/pad assembly that provides cooling to the sole of the hoof of an equine and, optionally, cooling under vacuum. It is also an apparatus for cooling both the sole and leg of an equine without the harmful effects of overcooling the legs.

In some embodiments the invention is, in broad aspect, an equine boot assembly comprising a boot having disposed therein a shock absorbing pad having a coolant circulation means in the pad. In one embodiment a heat transfer means is dispersed within the top portion of the pad to aid in the transfer of heat from the sole of a horse's hoof. In another the pad has a depression into which is placed a cooling bag through which coolant is circulated. In other embodiments the boot assembly also includes a leg cooling means that optionally uses coolant circulated through the pad coolant circulation means to circulate through cooling means for cooling of the leg.

In another embodiment the cooling boot assembly is also placed under reduced pressure.

In another embodiment the invention is a method of cooling the core temperature of an equine animal comprising placing at least one of its hooves inside a boot assembly comprising a boot having disposed therein an shock absorbing pad having a coolant circulation means therein and a flexible enclosure surrounding the hoof inside the boot, extending to a point up the horse's leg, and having means to make the enclosure relatively air tight around the leg, and means of reducing the pressure inside the enclosure, thereby placing the hoof under reduced pressure and passing coolant through the coolant circulation means and reducing the pressure inside the enclosure. In other embodiments the process includes cooling the leg of the animal as well as the hoof.

DETAILED DESCRIPTION OF THE INVENTION

Figure 1:
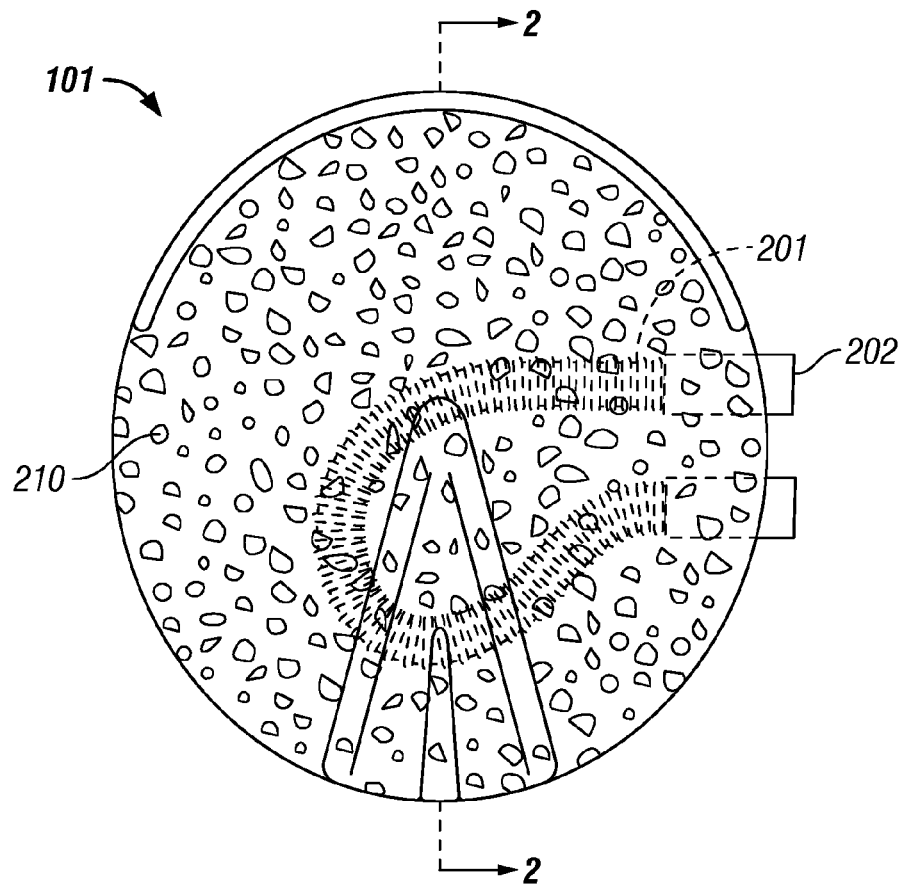
FIG. 1 is a top view of a pad of the invention showing a coolant coil and metal flakes in the pad.

Ideally, for cold therapy to be most successful as a true prophylactic for laminitis, a means of delivery is needed that can: (a) be applied simultaneously to all four of the horse's feet; (b) remain on the horse for extended periods of time (weeks instead of hours); (c) be light weight and allow the horse freedom of movement; and (d) be easily regulated and controlled. The present invention accomplishes all these conditions.

The boot/pad assemblies of this invention can be easily applied to all four equine hooves, can be used for extended times, is light weight and comfortable, and can easily be regulated and controlled.

In some embodiments cooling is achieved by a boot pad having heat conducting means into the top portion and a heat transfer means in the middle of the pad, such that the pad will be in contact with and cool the frog area of an equine hoof. Leaving the bottom portion of the orthotic pad without a heat conducting means provides insulation to prevent undue heat loss (cooling). In other embodiments the frog area is cooled by circulation of coolant through a cooling bag disposed in a depression of an orthotic pad. Unlike more conventional means, such as cooling the legs only, this invention provides an apparatus and means for applying cooling to the sole of the hoof, and optionally the leg, thus eliminating the disadvantages inherent in trying to achieve sufficient cooling by applying coolant to the legs only.

In one or more embodiments the equine boot pad assembly of the present invention uses versions of an equine boot and orthotic pad described in U.S. Pat. No. 7,178,321, issued Feb. 20, 2007, U.S. Pat. No. 7,445,051, issued Nov. 4, 2008, D565256, issued Mar. 25, 2008 and U.S. patent application Ser. Nos. 11/652,187 filed Jan. 11, 2007 and 12/284,925 filed Sep. 24, 2008, all of which appropriate portions are incorporated herein by reference.

The Preferred Boot/Pad Assembly

The basic features of the boot and pad useful in the assembly of this invention are summarized below.

The boot/pad assembly comprises a flexible boot and shock absorbing orthotic pad disposed inside and at the bottom of the boot. A version of the pad and boot as described in the patent and patent applications noted above is adapted to provide a coolant circulation means inside the pad and heat transfer means in the top portion of the pads or a cooling bag disposed in a depression of a pad (as described below).

The Boot

In broad aspect the boot of some embodiments of the invention comprises an upper portion made from flexible material shaped to fit the hoof of an animal. See FIG. 5. In general a suitable boot has a front, sides, rear and bottom; the front slopes back and upward, the sides are lower than the front and rear so that when the front and rear are pulled together there is an opening in the sides. There is a fastening means at the top front and rear to fasten the front and rear together around the leg and hoof of a horse. In one aspect the bottom is attached to a sole plate comprising a molded elastomer base entirely circumscribed by a peripheral wall (or sides) defining a receiving area sized to fit over (or under) the bottom of the upper portion.

The sole plate is preferably a separate molded piece and is attached to the bottom of the fabric upper. The sole plate helps to hold the boot in position on the hoof, and if walled around the entire circumference it prevents the hoof sliding forward or rearward while in use. Moreover, the sole plate is important in confining the orthotic pad in place. If a relatively "soft" pad is used (as is often desirable) the weight of the horse will flatten the pad and, if there were an opening in the sole plate the pad would be extruded out the opening. In this case it is especially important that the bottom circumference of the boot be sufficiently strong to contain the soft pad when it is squeezed outward by the pressure of the horse's hoof. By having the sole plate wall entirely surrounding the circumference the pad is held in place and will conform to the shape of the hoof—and adapt to the shape of the hoof as the horse moves. This allows the horse to find the best natural balance position—similar to the effect of having the horse stand in loose sand. The ability to achieve natural balance is especially important for horses with injured or diseased hooves.

It is preferred that the sole of the boot have a solid bottom to prevent the hoof from being in direct contact with the ground. This keeps the hooves cleaner and helps to prevent contamination leading to infection and/or injury.

In a preferred embodiment the bottom of the sole plate is sloped upward in the front at an angle of about five (5) to thirty (30) degrees from the bottom plane. The slope begins at a point on the bottom of the sole plate twenty (20) to forty (40) percent of the length from front to rear of the sole plate. The point of beginning is preferably about one third (⅓) of the distance from the front of the length of the sole plate. This angled sole plate allows the hoof to rock forward and backward without undue pressure on the hoof. When the horse walks the boot will "break-over" in a natural way, preventing abnormal pressure on the hoof. This rocker effect is well recognized as beneficial and there are a number of commercial products, such as the "clog" shoe and other devices designed to "rock" with the shift in body weight of the horse, allowing it to achieve a "natural balance". This is especially helpful for horses with sore or damaged hooves.

The sole plate is preferably molded of polymeric elastomer material or hard rubber (having the consistency and hardness to approximate automobile tires). Thermoplastic polyurethanes (TPUs) are suitable materials for the base plate. It is preferred that thermoplastic polyurethanes of about fifty-five

(55) to seventy-five (75) Shore A hardness be used, with Shore A hardness of sixty-five (65) to seventy (70) being especially suitable. Other polymer materials with characteristics similar to thermoplastic polyurethanes are also usable. Choosing these will be well within the ability of those skilled in the polymer art.

The Shock Absorbing Pad

Figure 2:
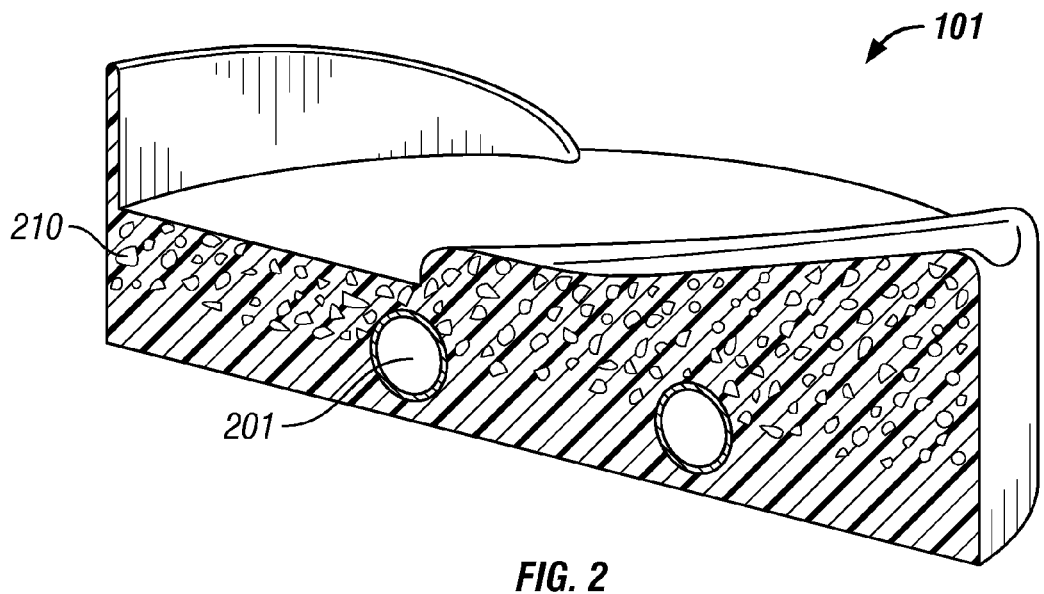
FIG. 2 is a section view of a pad of the invention showing metal flakes and an end view of a coolant circulating coil.
Figure 6:
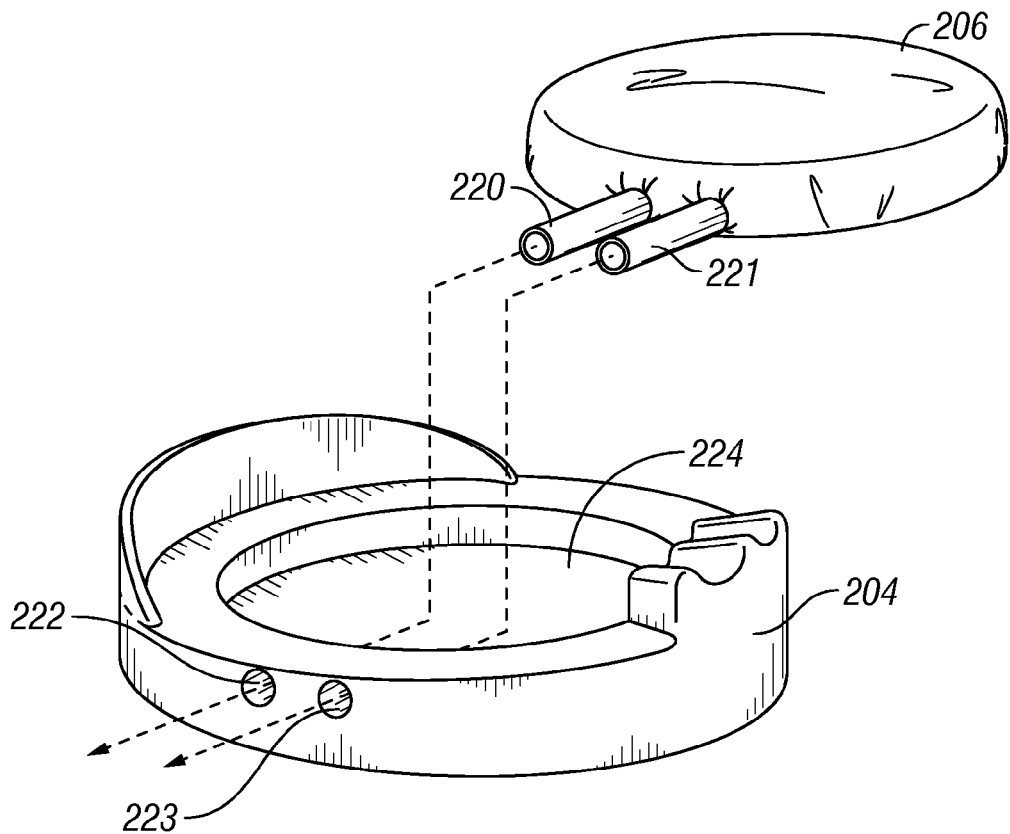
FIG. 6 is an isomeric view of a pad and cooling bag of an embodiment of the invention.
Figure 7:
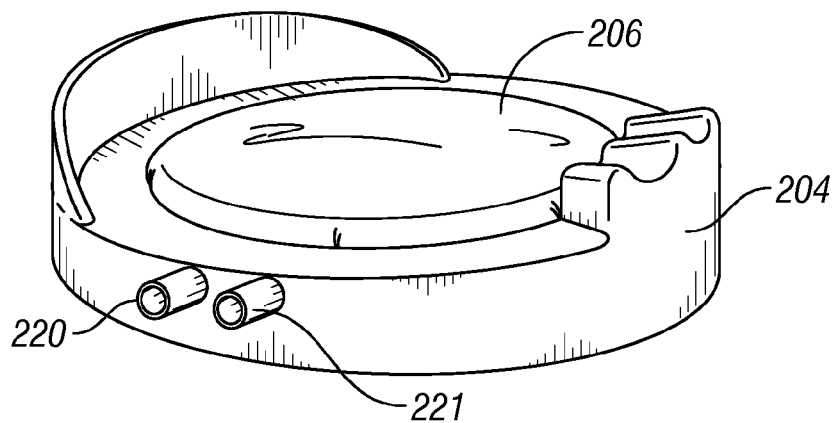
FIG. 7 is another isomeric view of a pad and cooling bag of an embodiment of the invention.

The base of the shock absorbing orthotic pad (FIGS. 1 and 2 are top and section views of a pad, FIGS. 6 and 7 are special versions) is generally shaped to approximate the shape of the animal's hoof-print and to fit into the boot. This pad, made of shock absorbing material, can be easily trimmed to conform to the hoof of the individual animal on which it will be used.

In one embodiment, on the backside of the base, opposite the ridge, is a frog support. This is a triangular projection (FIGS. 2, 6 and 7) above the surface of the base. This triangular projection is designed to approximately correspond to the shape and location of the frog of a horse's hoof. It has been found that the height of the frog support from the sole is very important to provide adequate uniform pressure as well as cushioning of the hoof. This frog support provides increased blood flow to the leg of the animal. The function of the triangle projection is to contact the frog during use, to provide a kind of massage to the frog of the hoof. Thus, blood circulation is stimulated and stress on the animal's legs and tendons are relieved. It is well known that the hoof frog acts somewhat as a blood pump. See for example, U.S. Pat. No. 4,981,010 where it is stated "The horny frog (58) is very elastic and acts as a shock absorber and as a second heart to the horse. As the hoof is pressed against the ground, old blood is forced up and out of the foot. When the hoof is lifted off the ground, the elastic frog (58) springs back, letting new blood into the foot." The frog support aids in this blood circulation. It is this pumping action of the frog that makes the cooling of the sole of the hoof especially effective.

In other embodiments, the pad will not have the triangular projection or the front projection. When used with a horse that has an abscessed or injured frog it may be desirable to use a pad without the frog support. Also, the improved sole plate of the boot makes it possible to eliminate the front projection for some applications. However, even without the frog support the front ridge projection (FIGS. 1, 2, 6 and 7) is often useful, especially for a horse with a severely injured or damaged hoof. At times it is necessary to resection (remove the front hard hoof surface) a horse's hoof if it is damaged or diseased. Such is the case with advanced laminitis. In such cases the soft front support ridge provides extra comfort to the hoof, especially if the pad is wedge-shaped (sloped) in a way that forces the front of the hoof downward. It is the burden of the pad base to supply the bulk of the support for the animal. The frog support is an aid to stimulation of the frog and is not the principal means of supporting the hoof. In this way, the present invention differs from previous frog support shoes or pads. An advantage of the relatively large and soft pad of the present invention is that it enables the horse to adjust the position of its hoof to the most comfortable position.

It has also been found that the shape of the pad is of special importance. Round pads have been found to not perform well in actual use; they tend to rotate in the boot. An elliptical shaped pad is desirable to maintain consistent fit and to prevent rotation of the pad in use. The base of the pad is made of any suitable elastomeric polymer material that provides flexibility, shock absorbency, some degree of elasticity, resilience and has dimensional stability. Polyvinyl chloride (PVC), polysilicone and similar elastomers well known to those in the art are also suitable. In a preferred embodiment, the base is constructed of a cast polyurethane elastomer. For example, polyurethane casting elastomer having a Shore A hardness of from about ten (10) to about seventy (70) is suitable. It is preferred that the base be of about twenty (20) to seventy (70) Shore A hardness and the support be of about eight (8) to fifty (50) Shore A hardness. In some situations very soft pads are desirable. These will generally be thicker than harder pads and will have a Shore 00 hardness of about five (5) to seventy (70).

In another important embodiment the base of the pad is made of components of different densities or hardness, herein referred to as a dual density pad. This pad has a base, for example, comprising a front component of shock absorbing material of lower hardness than a rear component, the front component comprising the forward twenty (20) to forty (40) percent of the length from front to rear of the pad and the rear component comprising twenty (20) to forty (40) percent of the length of the base from front to rear, wherein the two components overlap in the center of the base that is not occupied solely by the front or rear component. A very useful pad is made with the front component comprising about one third (⅓) of the length, the rear component comprising one third (⅓) of the length, and one third (⅓) overlap. It is also sometimes desirable to reverse the dual components with the harder portion in the front and the softer in the rear.

A very suitable dual density pad will be made of a polyurethane elastomer, the front component having a Shore A hardness of less than twenty (20) and the rear component having a Shore A hardness of between twenty (20) and forty (40). More desirably, the front would have a Shore A of five (5) or less, and the rear component a Shore A of about twenty-eight (28) to thirty-two (32). As with the single density pad, there is also a need for pads having softer front components, for example, having Shore 00 hardness of five (5) to about seventy (70). Elastomers, such as polyurethane, can be formulated in a wide range of rebound resiliencies.

For the pads of this invention it is preferred that the pad material have low rebound resiliency, generally lower that twenty-five (25) percent, and more desirably between two (2) and ten (10) percent.

FIGS. 6 and 7 illustrate a special pad in which there is a depression 224 in the pad to receive a cooling bag 206. The top sides of the pad are disposed under the outer hook and give support to the hoof. The cooling bag, 206, will give some support to the center of the hoof.

FIGS. 1 to 4 illustrates the way a pad is adapted for use in the present invention. Excessive cold applied only to the leg, as by cooling wraps, etc, can result in tightening or stiffening of the muscles and tendons and alone is not very efficient in cooling the internal temperature of the horse. Over-cooling of the leg can delay loosening of the muscles and tendons. Cooling of the frog area of the hoof is more effective than cooling of the leg alone. In one embodiment it is expedient to cool both the frog area and the leg as explained below. Since there are many blood vessels in the leg area, particularly in the areas around the coronet band just above the hoof, additional cooling in this area can be very effective. The present invention eliminates the ill effects of leg cooling by applying cooling to the frog area of the hoof where blood flow is greatest and optional cooling of the leg area with less cold coolants.

In general the desired reduction in blood temperature will be from about one (1) to eight (8)° F. and more preferred from about one and a half (1.5) to three and a half (3.5)° F. It has been reported that the optimum hoof cooling will cool the hoof to about thirty-two (32)° F. To achieve this hoof temperature efficiently it is necessary that the coolant be considerably cooler, generally in the range of about ten (10) to negative twenty (−20)° F.

The apparatus and method of this invention applies cooling (and optionally reduced pressure) to the sole and frog of the hoof and optionally the lower leg. Cooling of the sole and frog results in rapid cooling and does not result in stiffening the muscles and tendons. Since the frog acts like a blood pump the flexing of the frog results in tremendous blood flow through the sole of the hoof facilitating rapid cooling of the blood. Applying reduced pressure aids in the cooling and reduces vascular restriction that normally results from cooling the vessels.

Figure 3:
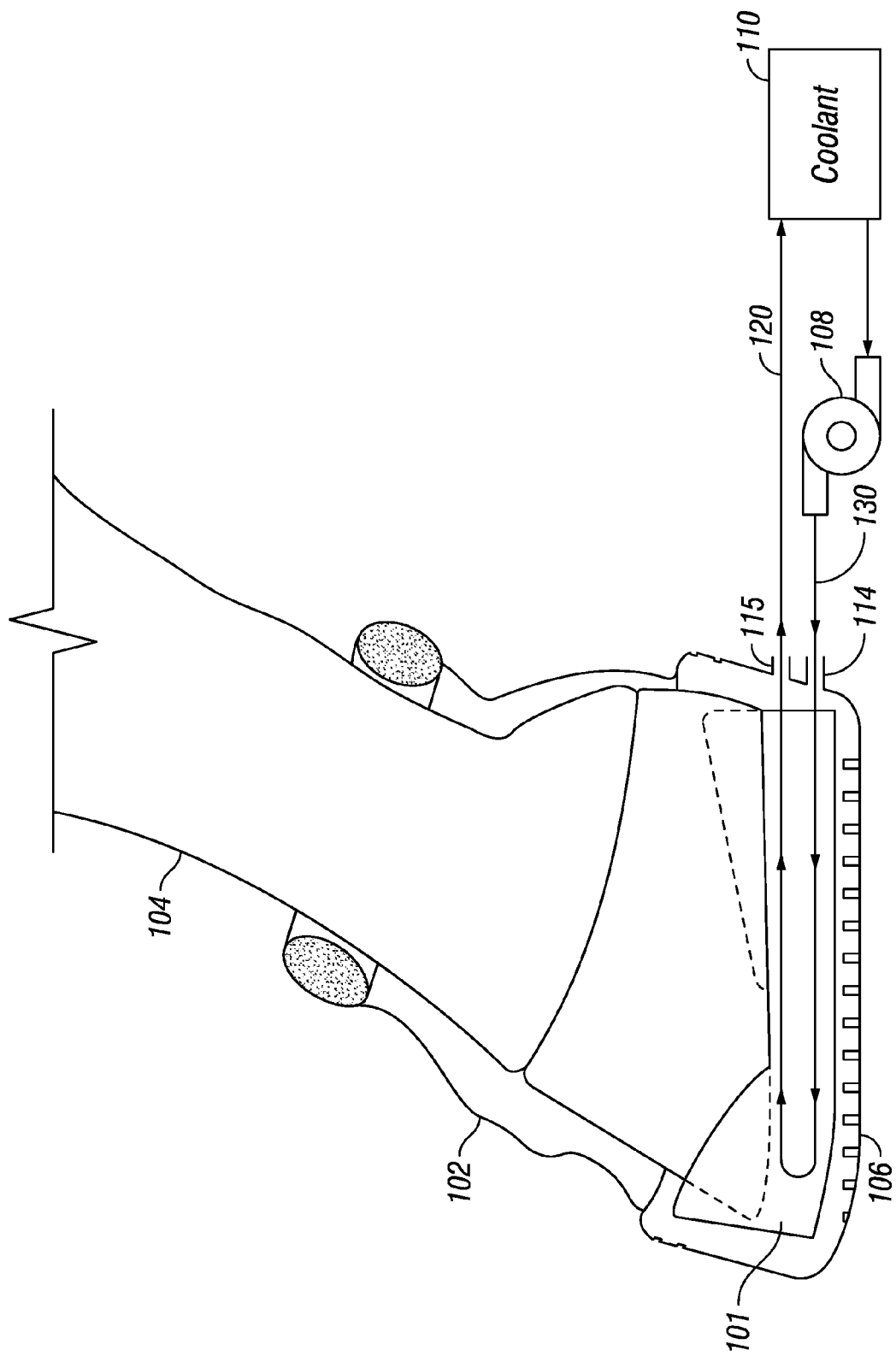
FIG. 3 is a schematic representation of an equine leg inside a boot of the invention showing coolant circulation.

Therefore, in one embodiment, there is disposed inside an shock absorbing pad a means, 201 and 202 of FIG. 1, for conveying coolant from an inlet, external of the boot, to an outlet, external of the boot. This is illustrated in FIG. 3 where 104 is the leg of the equine, 102 is the fabric boot with a base 106. Part 101 is an orthotic shock absorbing pad having a cooling means disposed therein. Coolant from coolant container 110 is circulated by pump 108 through line 130 and returned to the coolant reservoir 110 by line 120. The coolant passes by conduit through the boot port 115 and returns by the conduit through 114. The coolant conveying means inside the boot pad must be capable of carrying sufficient coolant to reduce the temperature of the pad and ultimately, the horse's hoof in the area of the frog.

Figure 4:
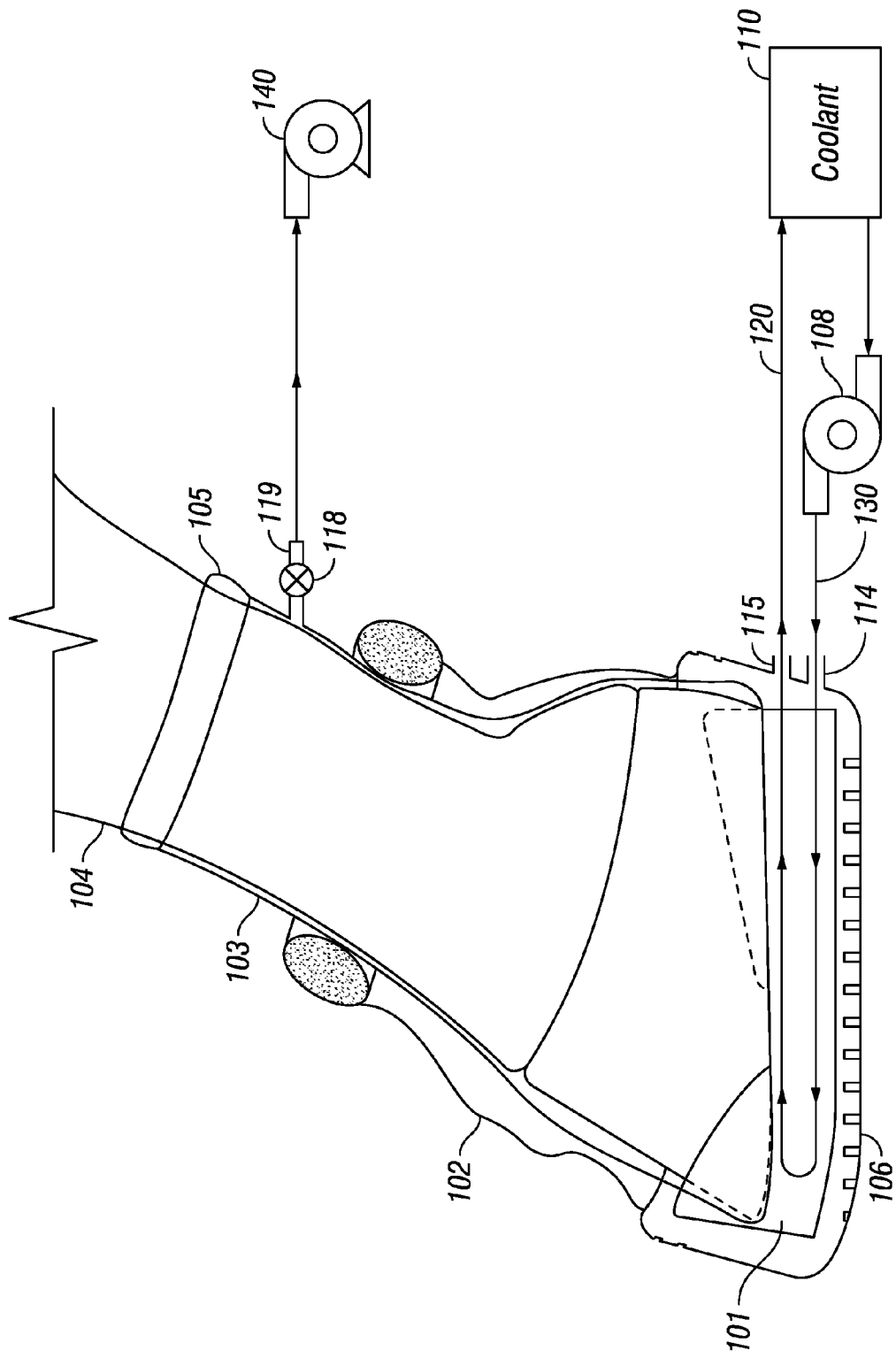
FIG. 4 is a schematic representation of an equine leg inside a boot of the invention showing coolant circulation and a vacuum enclosure.

FIGS. 2 and 4 illustrate one embodiment of the heat transfer means—a coil which can be molded into an shock absorbing pad through which coolant can be circulated. Part 202 in FIG. 1 is a connecting means that will fit through holes in the side of the fabric boot. Conduits are connected to the coil connector on the exterior of the boot to allow for connecting conduit, 120 and 130 in FIG. 4, to circulate coolant through the coil. The conduits are preferably flexible, as for example, silicone, polyethylene or polypropylene, vinyl, nylon, PVC, styrene and the like. The coolant reservoir is preferably a flexible bag with a battery operated pump disposed inside. With flexible conduit, portable reservoir and battery operated pump the entire system may be carried on the equine for complete portability and minimum interference with movement. Portability is not essential to the present invention and the reservoir may be stationary with an electric pumping means if desired.

Figure 5:
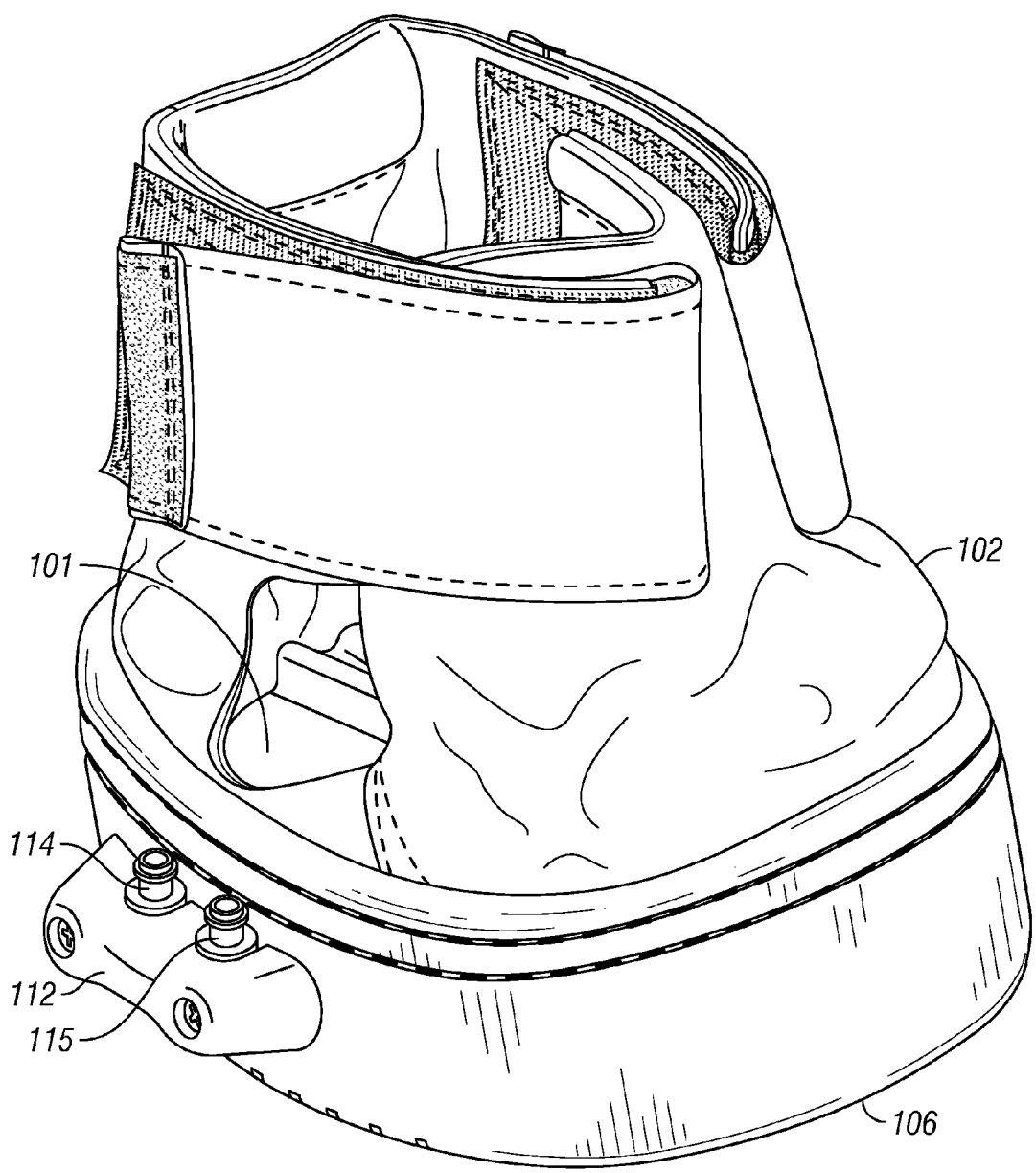
FIG. 5 is an isomeric view of a boot showing the coolant inlet and outlets.

Attaching the conduit through the side of the boot to a flexible conduit from a pump, 108, allows coolant to be pumped through the coil or cooling bag to regulate cooling. FIG. 5 shows a preferred fitting on the side of a boot. Part 112 is a rubber bumper that holds angled quick-connect fittings, 114 and 115 (that are screwed into the coil fittings 202 in FIG. 1). Conduit leading from the pump is attached to one of the quick-connect fittings and conduit to return the coolant to the reservoir into the other.

The coil (201 in FIG. 1) is shaped so that when disposed within the shock absorbing pad it will not be directly under the frog of the hoof. The coil as shown will be around the bottom circumference of the frog, not directly under it. The pad may also be made of a conductive elastomer polymer or may be layered with a top layer of a heat conductive elastomer and the bottom of a non-conductive polymer. The circulation means may also be a flat panel with a maze of channels to carry a coolant. See, for example, Cold Plates supplied by Aavid Thermalloy 70 Commercial St. Concord, N.H. 03301. These plates can be adapted to fit into the mid-section of an shock absorbing pad to supply a suitable coolant circulation means. Circulation paths may also be molded into the elastomer pad. Other means will be readily apparent to those skilled in the art.

In order to provide a means of heat transfer in the pad, metal particles or flakes (210 in FIGS. 1 and 2) are dispersed into the top portion of the pad—the side next to the hoof—of the pad to conduct heat from the hoof to the coolant circulation means, thereby cooling the hoof. By dispersing metal particles only into the top portion of an shock absorbing pad, the bottom portion remains an insulator, thereby increasing the efficiency of coolant heat transfer from the hoof to the coolant. The metal particles may be small chips, irregular particles, flakes, or the like. Textured particles are useful as they will be have greater surface area per unit of weight and thus have greater heat transfer properties and better adhesion to the pad. In general, the size of the particles is from about one sixty-fourth ($1/64$) to three sixteenths ($3/16$) inch diameter and flakes are about one sixty-fourth ($1/64$) to one sixteenth ($1/16$) inches thick and up to about one half ($1/2$) inch across. The size and density of the metal particles in the material of the pad will be a balance between conductivity and structure. The more particles present the better the heat conductivity, but too many particles will destroy the integrity of the pad and/or make it harder than desirable. However, it is important that the particles be of such size and density that most (or at least many) actually touch each other to adequately promote heat transfer. By simple experimentation, optimum numbers can easily be ascertained. About twenty (20) to seventy (70) percent metal by volume is appropriate.

Copper, aluminum and iron particles, flakes, or chips are useful. Aluminum is lightweight, inexpensive and excellent heat conductors. Copper particles are desirable since copper is a good heat conductor, lightweight and has been shown to have therapeutic effects. See for example, U.S. Pat. No. 4,961,933 where it is said "Dry pulverized copper has also been used for rheumatism in the wearing of pads containing the copper and other ingredients . . . . Such a teaching can be found in U.S. Pat. No. 92,065, issued Jun. 29, 1869, and in U.S. Pat. No. 55,234, issued Jun. 5, 1866."

If the particles are magnetic, they will be doubly beneficial—providing good heat conductivity and a beneficial magnetic field to the underside of the hoof. Magnetic particles will, of course, be iron or an iron compound. It has been reported that the application of a magnetic field to an injured member will aid blood circulation and promote healing. See U.S. Pat. No. 4,587,956, which discusses the beneficial effects of magnetic treatments and U.S. Pat. No. 6,139,486 wherein it is said "Magnetic field therapy is known to stimulate the circulation of blood, improve the oxygen consumption of blood cells, and reduce inflammation and fluid retention. These attributes are believed to promote healing and to reduce pain in those areas of the body where the magnetic field therapy is applied." See also U.S. Pat. No. 6,062,008.

The particles or flakes are dispersed in the portion of the pad around the sides of and above (towards the horse's hoof) the coolant circulation means as illustrated in FIGS. 1 and 2.

In another set of embodiments of the invention a pad 204 illustrated in FIGS. 6 and 7 has a depression 224 to allow insertion of a cooling bag 206. The depression has a minimum depth of approximately one fourth (0.25) inch (from surface of the pad) and is generally centered in the pad so as to leave at least about one half (0.5) inch of pad surface around the depression. This pad space is to provide support of the equine hoof and may be as wide (from depression to the edge of the pad) as one and one half (1.5) inches and depends upon the size of the pad (to accommodate different size hooves) and the desired support surface for the hoof.

The cooling bag, 206, has an inlet 220 and outlet 221 for circulation of coolant. The cooling bag may have baffles inside to more evenly circulate coolant to maintain a better distributed cooling surface against the frog area of the hoof. The cooling bag/pad assembly shown eliminates the need for the heat transfer metal particles in the pad, however copper and/or magnetic particles are optionally included in the pad as in the pads previously described. Coolant is circulated to the cooling bag in the same way as illustrated for the cooling pad—as illustrated in FIGS. 3 and 4. Conduits from a coolant reservoir 110 will be connected to conduits 220 and 221 for circulation of coolant.

The pad as shown has holes in the side 222 and 223 for the coolant conduits 220 and 221 to pass through. Instead of holes there may be cuts in the side of the pad to accommodate the conduit. The pad is generally the same as previously described but with a depression 224 in the top center. The range of suitable densities and construction materials for the pad 204 is basically the same as for pad 101 above. As explained above, the front ridge is useful but not essential to the invention, as is the partial frog support. The cooling bag is sized to fit within the pad's depression and is constructed of a flexible polymer material capable of withstanding the pressure of the weight of a horse's hoof—it needs be reasonably tough. Elastomeric polymers include Teflon™, Ultra High Molecular Weight (UHMW) polyethylene, some polyurethanes and the like. Choosing a suitably tough polymeric material is well within the skill of one skilled in the art of practicing this invention.

Figure 9:
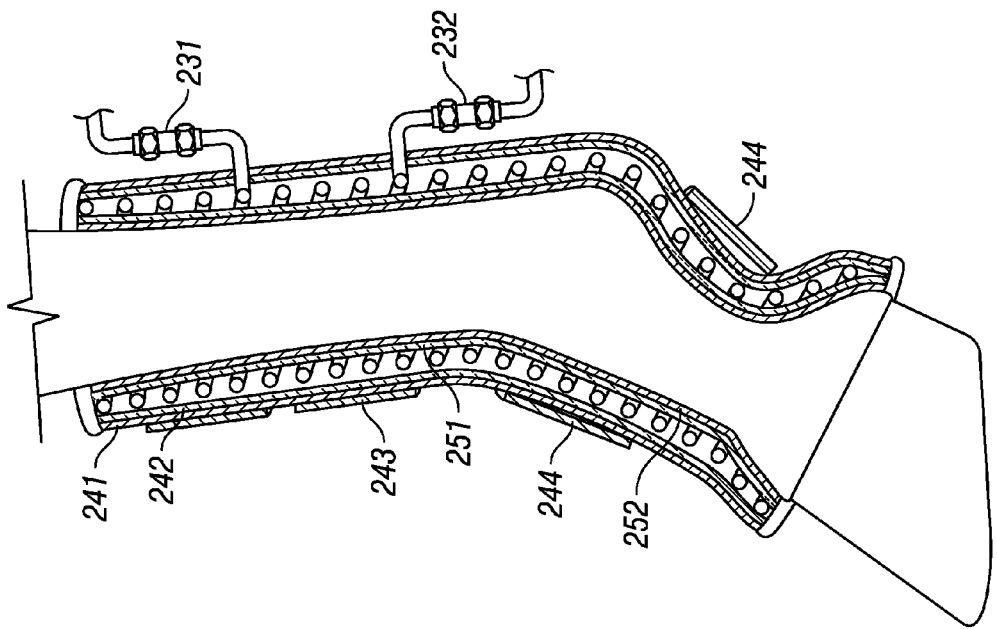
FIG. 9 is a side view of the leg wrap of an embodiment of the invention.
Figure 8:
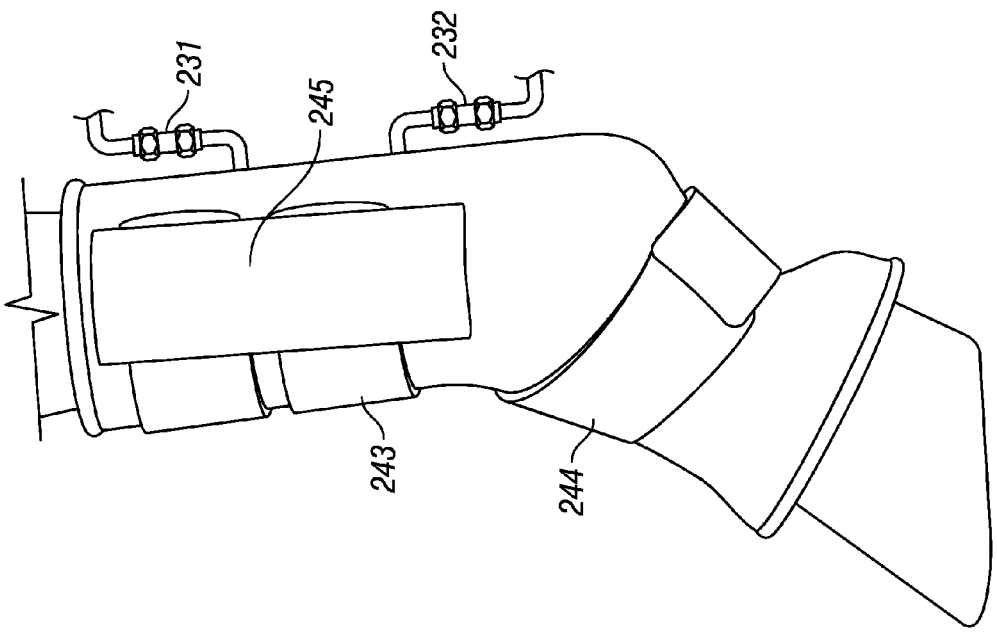
FIG. 8 is a side cut away view of a cooling leg wrap of an embodiment of the invention.

In other embodiments the frog area cooling means are combined with leg cooling means. A coolant leg wrap is illustrated in FIGS. 8 and 9. FIG. 8 shows the leg wrap having an inlet (to a coil or coils inside the wrap) 232 and outlet 231—this is seen more clearly in FIG. 9. The wrap has fastening means 244, 243 and 245 to secure it around the leg of a horse. FIG. 9 shows a cross section—the wrap comprises a flexible outer layer 252 and 241. Insulation 251 is provided on the leg side of the wrap and insulation 242 on the outer side of the wrap. In a preferred embodiment there is a pocket or series of pockets between the layer 252 and layer 242. These pockets allow additional insulation sheets to be added to moderate the temperature on the surface of layer 252 and therefore the equine leg. The coils connecting to inlet 232 and outlet 231 are disposed inside the wrap. Various fastening means may be used in the leg wrap of the invention, such as snaps, ties, buttons, buckles and preferably hook and loop, Velcro™, straps.

The insulation on the leg side protects the leg from excessively cold circulating coolant and the outside insulation prevents undue ingress of heat from the outside. The insulation is flexible and preferably of high efficiency so that it is not excessive bulky. Sheets of additional insulation may be placed in pockets between the layer 252 and layer 242. While selecting a suitable insulating material is well within the skill of one skilled in the art, an Aerogel insulation Pyrogel™ available from Advanced Thermal Corp. is especially suitable because of its outstanding insulating properties and toughness. In operation coolant would pass from the frog area pad 204 by conduits 220 and 221 or pad 101 by conduit 202.

Control of the temperature of the coolant in contact with the leg is important. Generally the coolant temperature against the leg surface, should not be much below thirty-two (32)° F. This is why the insulation 252 is provided. Much colder coolant is desirable for the frog area. The frog area will not be adversely affected by very cold coolants and the range of coolant temperatures suitable is explained above. Since the coolant in contact with the leg needs to be more moderate; however, sufficient insulating means 251 is provided to ensure that the inside cover of the leg wrap does not drop below about thirty-two (32)° F.—no lower that about twenty-eight (28)° F. In the embodiment with pockets additional insulation is added to achieve the desired temperature on the leg surface. The amount and nature of additional insulation depends upon the temperature of the coolant, the circulation rate and the initial insulation disposed in the leg wrap. For dual frog/leg cooling circulating coolant may be in the range of about ten (10) to negative twenty (−20)° F.

Coolants

Suitable coolants should have good thermal conductivity, a low flash (or vaporization temperature) point, be non-corrosive, inexpensive and readily available. Some useful coolants include, but are not limited to: water, iced water, ethylene glycol, propylene glycol, methanol/water, ethanol/water, calcium chloride solution, potassium formate/acetate solution. Some of these can be used down to negative forty (−40)° F. and have superior conductivity. It is not likely that more exotic refrigerant coolants will be required. The temperatures to which the hoof can be cooled are not extreme—e.g. it is unlikely that the temperatures below about negative twenty (−20)° F. will be desirable.

Coolants may be suitably cooled by placing ice, coolpacks, dry ice or the like in the coolant reservoir to obtain the desired temperature. Of course, the coolant may be continuously refrigerated by a portable refrigerator, but doing so reduces portability of the coolant boot.

Circulation of coolant will be sufficient to maintain the top of the cooling pad or cooling bag at the desired temperature during use. This will depend upon the temperature of the coolant, the heat transfer ability of the heat transfer means disposed in the pad or the cooling bag, and the heat conductivity of the pad. Proper circulation parameters can easily be determined by experimentation with each individual pad design.

Vacuum

In another set of embodiments there is provided a means of applying both the cold sole therapy and a vacuum on the equine's hoof. See FIG. 4. It is known that application of vacuum (pressure reduced below atmospheric pressure) can also be beneficial during cold therapy. See U.S. Pat. No. 6,656,208 and U.S. Pat. No. 7,160,316 B2 and related patents which disclose the use of cold therapy under reduced pressure in mammals. Vacuum may also be beneficial in healing wounds in the hoof. See the web site http://en.wikipedia.org/wiki/VAC_Therapy for application of vacuum therapy to humans.

Reduced pressure (vacuum) can be achieved, in one embodiment, by enclosing the horse's hoof inside a substantially air tight flexible enclosure, bag or sock (103 of FIG. 4) that will fit inside the boot assembly described above. The bag is secured around the leg (105 of FIG. 4) above the boot and has an outlet fitting 119 and valve 118 that allows air to be removed with a pump 140 to pull a vacuum on the hoof inside the boot. A battery operated portable vacuum pump is preferred. Thus, the sole of the hoof is cooled under vacuum. The vacuum aids, inter alia, to overcome vascular constriction caused by the cooling. This allows better and faster blood flow which increases the speed and effectiveness of cooling to achieve the desirable core cooling. Generally the reduced pressure will be sufficient to alleviate vascular constriction but not great enough to cause a tourniquet effect around the leg of the animal. Reduced pressure from about twenty (20) to seventy-five (75) mmHg (from ambient) are preferred and thirty (30) to forty (40) mmHg being most preferred.

The vacuum bag may be secured around the leg, for example, by taping, or by an elastic band (105 in FIG. 4). In one embodiment the sealing band 105 is fitted with an inlet means and a valve so that the seal band may be inflated to secure the top of the bag to the leg. This means has the advantage of being able to be adjusted properly to prevent a tourniquet action on the leg but provide an air tight seal.

In another embodiment, the bag will have a layer of open pore foam disposed in it sufficient to fit around the top of the hoof and around the leg. The layer of foam will hold the bag away from the leg and hoof, allowing air flow from the bag and preventing the bag collapsing when the pressure is reduced.

Methods of the Invention

In one aspect the invention is a method of reducing the internal or core temperature of an equine animal. Reducing the internal temperature is useful to rapidly cool overheated horses when they are exercised or transported or stalled under hot climate conditions. Moreover, it is also known that reducing the internal temperature will enhance the performance of equines during competitive activities such as racing, cutting horse competition, barrel racing and the like. Additionally, it is known that cooling the leg and hoof of an equine is effective in treating laminitis.

The method comprises placing at least one of an equine's hooves inside a boot assembly comprising a fabric boot having disposed therein a shock absorbing pad having a coolant circulation means therein.

In another embodiment the method comprises placing at least one of an equine's hooves inside a boot assembly comprising a fabric boot having disposed therein a shock absorbing pad having a coolant circulation means therein, and a flexible enclosure surrounding the hoof inside the boot, extending to a point up the horses' leg, and having means to make the enclosure relatively air tight around the leg, and means of reducing the pressure inside the enclosure, thereby placing the hoof under reduced pressure and passing coolant through the coolant circulation means and reducing the pressure inside the enclosure and letting the hoof remain in the boot for sufficient time to achieve the reduction of temperature desired.

In another embodiment the method will comprises placing at least one of an equine's hooves inside a boot assembly comprising a fabric boot having disposed therein a shock absorbing pad having a coolant circulation means therein with the addition of a leg cooling means through which the circulating coolant for the pad will also pass. In one embodiment the leg cooling means is a flexible wrap having pockets for placing insulation sheets to achieve a desired temperature on the equine leg. Thus, when a coolant and circulation rate is established the temperature on the surface of the leg wrap that is will be in contact with the leg is measured. If it is too low, sheets of insulation will be added until the desired temperature is achieved.

The conditions of temperature and duration of treatment for each of these embodiments and reduced pressure level are detailed above in the description of the equine boot of the invention.

The use of a boot assembly described above is especially effective if the sole of the boot is sloped as described and the pad is soft and deep. This allows effective cooling of the hoof, leg and blood of the equine and also provides a comfortable, healing natural balance to the animal's stance.

Example

Drastic cooling of the pad has been demonstrated in bench tests and the following example illustrates the efficiency of an embodiment of the invention. Thermographic images of the hoof of an aged champion cutting horse showed heat due to weight transfer. Initially the foot was in the ninety (90)° F. range. A non-circulating coolant pad was placed under the frog area of the hoof and a dramatic temperature reduction was obtained after only fifteen (15) minutes. This demonstration clearly shows that cooling the sole of the hoof can be produce rapid cooling of the core temperature.

In the foregoing specification, the invention has been described with reference to specific embodiments thereof. It will, however, be evident that various modifications and changes can be made thereto without departing from the broader spirit and scope of the invention as set forth in the appended claims. The specification and drawings are, accordingly, to be regarded in an illustrative rather than a restrictive sense. Therefore, the scope of the invention should be limited only by the appended claims.

The invention claimed is:

1. An equine boot assembly comprising a boot for placement on an equine hoof having disposed therein a pad having a coolant circulation means disposed therein, wherein the coolant circulation means is enclosed in a manner to allow coolant to circulate without direct contact of the coolant with the pad or equine hoof.

2. The boot assembly of claim 1 wherein the pad has a top, edge and bottom and has a heat transfer means disposed in its top comprising particles or flakes of metal selected from a group consisting of iron, magnetized iron, copper and aluminum embedded therein to allow heat to be transferred from the coolant circulation means to the equine hoof.

3. The boot assembly of claim 1 wherein the coolant circulation means is a metal coil placed within the pad.

4. The boot assembly of claim 1 wherein the pad has a top, edge and bottom and has a depression in the top with a cooling bag disposed therein in which coolant may be circulated in a manner to allow coolant to circulate without direct contact of the coolant with the pad or equine hoof.

5. The boot assembly of claim 4 wherein the depression is at least one quarter inch below the top of the pad and the pad depression is no closer to the edge of the pad than about one half inch.

6. The boot assembly of claim 1 wherein there is also provided a leg cooling means having a conduit for circulation of the coolant.

7. The boot assembly of claim 6 wherein there is provided insulating means between the conduit and an equine leg to prevent over-cooling of a surface of the equine leg.

8. The boot assembly of claim 1 wherein the pad in the boot and a lower leg of an equine are enclosed in a flexible enclosure with means to provide a seal around a leg and from which enclosure air can be removed to achieve a sub-atmospheric pressure inside the enclosure.

9. The boot assembly of claim 8 wherein an open cell foam is disposed between the enclosure and the leg of the equine to prevent collapse of the enclosure.

10. The boot assembly of claim 1 wherein the boot comprises an upper section made from flexible material, shaped to fit around a hoof of a horse and of a height to reach above the hoof of an equine, comprising a front, sides, and rear, a fastening means to fasten the front and rear together around an equine leg, and an elastomeric bottom section into which the upper section is disposed.

11. A method of cooling the internal temperature of an equine animal comprising placing at least one of its hooves inside a boot assembly comprising a boot having a pad with coolant circulation means disposed therein and circulating coolant through said coolant circulation means wherein the coolant circulation means is enclosed in a manner to allow coolant to circulate without direct contact of the coolant with the pad or equine hoof on which the boot assembly is placed.

12. The method of claim 11 wherein the pad has a top, edge and bottom and has a heat transfer means disposed in the top of the pad comprising particles of heat transferring metals embedded therein to allow heat to be transferred from the coolant circulation means to the equine hoof.

13. The method of claim 11 wherein the heat transfer means of the pad is particles or flakes of metal selected from a group consisting of iron, magnetized iron, copper and aluminum, and the coolant circulation means is a metal coil disposed within the shock absorbing pad.

14. The method of claim 11 wherein the pad has a top, edge and bottom and has a depression in the top with a cooling bag disposed therein for circulation of coolant means in a manner to allow coolant to circulate without direct contact of the coolant with the pad or equine hoof.

15. The method of claim 11 wherein there is also provided a leg cooling means having a conduit for circulation of the coolant and circulating the coolant through said coolant circulation means.

16. The method of claim 15 wherein the coolant circulated through the pad is also circulated through the leg cooling means and wherein there is provided insulating means between the leg cooling means and an equine leg to prevent over-cooling of a surface of the equine leg.

17. The method of claim 11 wherein the pad in the boot and a lower leg of the equine are enclosed in a flexible enclosure with means to provide a seal around a leg and from which air can be removed to achieve a pressure inside the enclosure below atmospheric and reducing the pressure therein.

18. The method of claim 11 where the boot comprises an upper section made from flexible material, shaped to fit around the hoof of a horse comprising a front, sides, and rear, a fastening means to fasten the front and rear together around a leg of a horse, and an elastomeric bottom into which the upper section is disposed.

* * * * *